US012678030B2

(12) United States Patent
Christensen et al.

(10) Patent No.: US 12,678,030 B2
(45) Date of Patent: Jul. 14, 2026

(54) ENDOSCOPE USING CAPSTAN PRINCIPLE

(71) Applicant: AMBU A/S, Ballerup (DK)

(72) Inventors: Martin Johst Christensen,
Copenhagen Ø (DK); Dylan Ilg, Inning
am Ammersee (DE)

(73) Assignee: AMBU A/S, Ballerup (DK)

( * ) Notice: Subject to any disclaimer, the term of this
patent is extended or adjusted under 35
U.S.C. 154(b) by 514 days.

(21) Appl. No.: 18/019,923

(22) PCT Filed: Aug. 10, 2021

(86) PCT No.: PCT/EP2021/072280
§ 371 (c)(1),
(2) Date: Feb. 6, 2023

(87) PCT Pub. No.: WO2022/034084
PCT Pub. Date: Feb. 17, 2022

(65) Prior Publication Data
US 2023/0309801 A1      Oct. 5, 2023

(30) Foreign Application Priority Data

Aug. 13, 2020    (DE) ..................... 10 2020 121 365.4

(51) Int. Cl.
A61B 1/005         (2006.01)
A61B 1/00         (2006.01)
(52) U.S. Cl.
CPC .......... A61B 1/0052 (2013.01); A61B 1/0057
(2013.01)
(58) Field of Classification Search
CPC .. A61B 1/0052; A61B 1/0057; A61B 1/00066
See application file for complete search history.

(56) References Cited

U.S. PATENT DOCUMENTS

| | | | |
|---|---|---|---|
| 3,897,775 A | 8/1975 | Furihata | |
| 4,483,326 A | 11/1984 | Yamaka et al. | |
| (Continued) | | | |

FOREIGN PATENT DOCUMENTS

| | | |
|---|---|---|
| DE | 2441222 A1 | 3/1975 |
| DE | 3214615 A1 | 12/1982 |
| (Continued) | | |

OTHER PUBLICATIONS

International Search Report and Written Opinion received for PCT
Patent Application No. PCT/EP2021/072280, mailed on Nov. 12,
2021, 11 pages.

(Continued)

*Primary Examiner* — Anh Tuan T Nguyen
*Assistant Examiner* — Rynae E Boler
(74) *Attorney, Agent, or Firm* — Faegre Drinker Biddle &
Reath LLP

(57) ABSTRACT

An endoscope and a method of assembling the endoscope,
the endoscope including a handle including a wire receiving
unit rotatably connected to an operating unit; a distal tip unit
configured to be inserted into a patient's body cavity; an
endoscope shaft connecting the endoscope handle and the
distal tip unit; and at least one steering wire, a proximal end
portion of which being held by or fixed to the wire receiving
unit, the steering wire being configured to be pulled by
rotating the operating unit, thereby tilting the distal tip unit
in at least a defined first direction, wherein the proximal end
portion of the at least one steering wire is wound around/on
the wire receiving unit for at least one full turn.

23 Claims, 5 Drawing Sheets

(56) References Cited

U.S. PATENT DOCUMENTS

| | | | |
|---|---|---|---|
| 2002/0143238 A1 | 10/2002 | Hino et al. | |
| 2008/0275302 A1* | 11/2008 | Hosaka | A61B 1/0052 |
| | | | 600/139 |
| 2009/0234186 A1 | 9/2009 | Lin et al. | |
| 2010/0082041 A1 | 4/2010 | Prisco | |
| 2011/0118550 A1 | 5/2011 | Tulley | |
| 2012/0220832 A1* | 8/2012 | Nakade | A61B 1/0057 |
| | | | 600/149 |
| 2012/0330287 A1* | 12/2012 | Yim | A61B 34/71 |
| | | | 606/1 |
| 2014/0088497 A1 | 3/2014 | Campbell et al. | |
| 2014/0257333 A1* | 9/2014 | Blumenkranz | A61B 34/71 |
| | | | 606/130 |
| 2015/0011830 A1* | 1/2015 | Hunter | A61B 1/0016 |
| | | | 600/118 |
| 2016/0338571 A1 | 11/2016 | Haraguchi | |
| 2016/0357006 A1 | 12/2016 | Koyama | |
| 2017/0354318 A1 | 12/2017 | Rogers et al. | |
| 2019/0192245 A1* | 6/2019 | Abbott | A61B 34/37 |
| 2019/0350440 A1 | 11/2019 | Leong et al. | |
| 2021/0338051 A1* | 11/2021 | Nielsen | A61B 1/0052 |
| 2022/0015847 A1* | 1/2022 | Kadokura | A61B 34/37 |
| 2023/0263376 A1* | 8/2023 | Lo | A61B 90/361 |
| | | | 600/109 |
| 2024/0315538 A1* | 9/2024 | Yi | A61B 1/005 |

FOREIGN PATENT DOCUMENTS

| | | |
|---|---|---|
| EP | 3103374 A1 | 12/2016 |
| GB | 2475364 A | 5/2011 |
| JP | 08-082749 A | 3/1996 |
| WO | 2016/188543 A1 | 12/2016 |

OTHER PUBLICATIONS

Search Report received for German Patent Application No. 102020121365, mailed on Apr. 9, 2021, 22 pages (11 pages of English Translation and 11 pages of Original Document).

* cited by examiner

ENDOSCOPE USING CAPSTAN PRINCIPLE

CROSS-REFERENCE TO RELATED APPLICATIONS

This application is a National Phase entry under 35 U.S.C. § 371 of International Application No. PCT/EP2021/072280, filed Aug. 10, 2021, which claims priority from and the benefit of German Patent Application No. DE 10 2020 121 365.4, filed Aug. 13, 2020; said applications are incorporated by reference herein in their entirety.

TECHNICAL FIELD

The present disclosure relates to an endoscope comprising a proximal endoscope handle comprising at least one rotatable operating unit, preferably a handle wheel, and at least one wire receiving unit, preferably a wire drum, the wire receiving unit being rotatably connected to the operating unit; a distal tip unit configured to be inserted into a patient's body cavity; an endoscope shaft connecting the endoscope handle and the distal tip unit; and at least one steering wire, a proximal end portion of which being held by or fixed to the wire receiving unit, the steering wire being guided from the wire receiving unit to the distal tip unit and being configured to be pulled by rotating the operating unit, thereby bending the distal tip unit in at least a defined first direction.

BACKGROUND ART

Endoscopes, including specialized instruments such as bronchoscopes, arthroscopes, colonoscopes, laparoscopes, gastroscopes and duodenoscopes, are well known from the state of the art and are used for visual examination and diagnosis of hollow organs and body cavities, as well as to assist in surgery, e.g. for a targeted tissue sampling.

Therefore, known endoscopes usually contain steering/control wires within so-called Bowden cables that are pulled and released to bend a bending section, such as a flexible shaft or at least part of a flexible shaft, in order to tilt the distal tip unit of the endoscope. The rotating forces being applied to the handle wheels by a user basically have to be transmitted into pulling forces acting on the steering wires in axial direction of the steering wires, i.e. the loads in the steering wires are transferred to the handle wheels within the endoscope handle. It is to be understood, that the connection of the steering wires to the handle wheels is essential for transmitting the rotating force from the handle wheel to the steering wire.

In a conventional endoscope, such as it is disclosed in US 2016/0357006 A1, this can be achieved by a chain attached to the ends of the steering wires passing over a sprocket attached to the handle wheel. Alternatively, in traditional bronchoscopes, each steering wire is guided around a stop of the handle wheel and returns parallel to a crimp.

In contrary thereto, in WO 2016/188543 A1, each steering wire is guided around the circumference of a wire drum or a roller/pulley and fixed by a press fit in a hole achieved by inserting a mandrel into the hole which the wire runs through, so the wire is squeezed between the mandrel and a wall of the hole. Alternatively, as shown for example in DE 2 441 222 A1 or DE 3 214 615 A1, the steering wires are guided around the wire drum and fixed on an axial end surface of the wire drum by fixing means, such as a clamping screw or a pin. A further example of a wire drum, on which steering wires are being fixed by axially inserted pins, is given in EP 3 103 374 A1. As an alternative it has been proposed to use wires directly attached to a pulley, but problems then exist with the management of the wires as they are unwrapped from, and re-wrapped to, the pulley to ensure that they remain free from tangles.

Further, the steering wires can be fixed to the wire drum by additional elements. For example, in GB 2 475 364 A1, the steering wires are guided around the wire drum within a groove extending in a circumferential direction of the wire drum, before being fixed to the wire drum by inserting an anchor element into this groove. This anchor element presses the steering wire to the wire drum, thereby preventing the steering wire from slipping around or off the wire drum.

A major drawback of the existing solutions is that the steering wires are bent or kinked when being fixed to the wire drum, which may compromise their strength. Another drawback is that the connection of the steering wire to the handle wheel, in particular to the wire drum, must withstand high forces during use, which cannot be ensured when bending the steering wire, thereby compromising the structural integrity of the steering wires or the wire drums, in particular for single-use endoscopes.

At this point, the expressions "distal" and "proximal" are defined for the whole application (including the description of the disclosure) as follows:

Distal: In the direction away from a user (toward the patient)

Proximal: In the direction toward the user (away from the patient)

SUMMARY

The tasks and objectives of the disclosure are to eliminate or at least reduce the disadvantages of the prior art. In particular, an endoscope having at least one steering wire being fixed to a wire drum and a distal tip unit of the endoscope, in order for a user to be able to steer/bend the distal tip unit when rotating a handle wheel being connected to the wire drum, is to be provided, wherein the structural integrity of the bending mechanism including the wire drum, the steering wire and the handle wheel can be ensured or improved, without bending or kinking the steering wire, when fixing it to the wire drum. Additionally, the bending mechanism and thus the endoscope handle may be manufactured with smaller dimensions, in order to improve usability and holding comfort.

The disclosure is based on the knowledge that due to interaction of frictional forces and tension, the tension on a wire wrapped around a cylinder is different on either side of the cylinder. A small holding force exerted on one side can carry a much larger loading force on the other side.

In other words, the present disclosure is based on the Capstan principle and involves the steering wire running around a cylindrical wire drum by at least one full turn, preferably at least two turns. The wire drum rotates around its center axis to tension a steering wire to effect bending of the distal tip unit. By running the wire around the wire drum, the wire fixing is relieved of some of the load which is instead transferred by friction to the wire drum. Further, the wire receiving unit comprises a first groove, a second groove and a third groove, the grooves extending in a circumferential direction of the wire receiving unit and guiding/accommodating two steering wires. In other words, the wire receiving unit includes a plurality of grooves extending in the circumferential direction of the wire receiving unit and guiding the at least one steering wire so that the at least one steering wire runs only once within each of the plurality of grooves.

According to the disclosure, the endoscope is accordingly configured/adapted, so that the proximal end portion of the at least one steering wire is wound on/around the wire drum for at least one full turn, i.e. at least 360°.

This configuration makes it possible to reduce the holding force of the steering wire fixing, which can thus be made smaller.

Advantageous embodiments are claimed in the dependent claims and are explained below.

In a preferred embodiment, two steering wires can be wound around on the wire receiving unit, so that when rotating the operating unit in a first circumferential, preferably clockwise, direction one of the two steering wires is pulled and the distal tip unit tilts in the defined first direction and when rotating the operating unit in a second circumferential, preferably counter-clockwise, direction opposite of the first circumferential direction, the other one of the two steering wires is pulled and the distal tip unit tilts in a second defined direction opposite of the first defined direction. Thus, by fixing two steering wires on the wire drum, the distal tip unit can be steered/bent in two opposite directions, i.e. in a bending plane being defined by the first and second direction, which enables improved maneuverability for the distal tip unit.

Additionally, in this regard, it can be conceivable, if the endoscope handle comprises two operating units and two wire receiving units, i.e. two operating units are arranged at the endoscope handle, and two wire drums are arranged within the endoscope handle. Thereby, each of the wire receiving units can have two steering wires wound on/around the same and can be connected to one of the operating units, so that the distal tip unit tilts in a first bending plane defined by the first defined direction and the second defined direction when operating one of the operating units and the distal tip unit tilts in a second bending plane, preferably perpendicular to the first bending plane, when operating the other one of the operating units.

According to a beneficial design of the disclosure, the at least one steering wire can be fixed to the wire receiving unit via a press fit connection. Thereby, at least one, preferably circumferentially extending, fixation hole is formed on the wire receiving unit, in particular in a block-shaped fixation protrusion of the wire drum, the at least one steering wire being fixed to the wire receiving unit by means of a mandrel or fixation pin inserted in said fixation hole such that the at least one steering wire and the mandrel form the press fit connection. When the at least one steering wire is fixed in the fixation hole by inserting the mandrel, wire bends are avoided, which increases the reliability of the at least one steering wire.

Further, the first groove can be arranged closest to a flange portion of the wire receiving unit, the third groove can be arranged farthermost from the flange portion and the second groove can be arranged between the first groove and the third groove, wherein one of the two steering wires runs around the wire receiving unit within the first groove and the second groove in the first circumferential direction and the other one of the two steering wires runs around the wire receiving unit within the first groove and the third groove in the second circumferential direction.

According to a further beneficial design of the disclosure, both of the two steering wires can enter the same circumferential direction among the first groove, the second groove and the third groove, in particular at diametrically opposed positions of the respective circumferential groove, and can transition/transfer to their respective own groove among the first groove, the second groove and the third groove when wound around/on the wire receiving unit.

Furthermore, in this regard, it is particularly preferred, when one of the two steering wires enters the first groove at a first position, e.g. twelve o'clock when viewing the wire receiving unit in axial direction, runs around the wire receiving unit for approximately a quarter turn within the first groove, transitions to the second groove and runs within the second groove for approximately a full turn before being fixed to the wire receiving unit, and the other one of the two steering wires enters the first groove at a second position, preferably diametrically opposed to the first position, e.g. six o'clock, runs around the wire receiving unit for approximately a quarter turn within the first groove, transitions to the third groove and runs within the third groove for approximately a full turn before being fixed to the wire receiving unit.

In other words, preferably both of the two steering wires enter the same (first) circumferential groove of the wire drum at diametrically opposed positions of the respective groove and transition to their respective own groove (e.g. the first steering wire transitions to the second groove, and the second steering wire transitions to the third groove, or the other way round).

Moreover, the one of the two steering wires and the other one of the two steering wires can transition from the first groove to the second groove or the third groove, respectively, within a transition zone being formed radially inside the fixation protrusion. This preferable configuration ensures that each steering wire is guided in a separate groove, i.e. the respective grooves are only occupied by a single steering wire.

In other words, in a specific embodiment, the present disclosure relates to an endoscope, the wire drum of which is provided with grooves preferably for each turn of the wire so that a groove is only occupied by a single wire. The wire can be fixed by running the wire around the wire drum in the grooves a number of times and then guiding the wire through a circumferential hole and back through another parallel fixing hole. A mandrel is then inserted into the last (fixing) hole to fix the wire.

Further, the present disclosure relates to a method of assembling an endoscope having: a proximal endoscope handle comprising at least one rotatable operating unit, preferably a handle wheel, and at least one wire receiving unit, preferably a wire drum, comprising a first groove, a second groove and a third groove, the grooves extending in a circumferential direction of the wire receiving unit and guiding/accommodating two steering wires; a distal tip unit configured to be inserted into a patient's body cavity; and an endoscope shaft connecting the endoscope handle and the distal tip unit. The method comprises the following steps:

Connecting a distal end portion of each of the two steering wires to the distal tip unit;

Guiding each of the two steering wires along the endoscope shaft to the endoscope handle;

Winding each of the two steering wires for at least one full turn around the wire receiving unit;

Tensioning each of the two steering wires by pulling the proximal end portion of the steering wire;

Fixing each of the two steering wires to the wire receiving unit.

Thereby, it may be particularly useful, when the method further comprises the steps:

Connecting two steering wires to the distal tip unit;

Guiding the two steering wires along the endoscope shaft to the proximal endoscope handle;

Winding one of the two steering wires around the wire receiving unit in a clockwise direction; and Winding the other one of the two steering wires around the wire receiving unit in a counter-clockwise direction.

Additionally, in a preferred embodiment, the method may comprise the steps:

Introducing the two steering wires in a first circumferential groove provided on the wire receiving unit;

Transferring/transitioning one of the two steering wires from the first circumferential groove into the second circumferential groove;

Transferring/transitioning the other one of the two steering wires from the first circumferential groove into the third circumferential groove;

Winding the one of the two steering wires around the second circumferential groove; and Winding the other one of the two steering wires around the third circumferential groove.

According to a beneficial configuration, the method may further comprise the following steps:

Overlapping the two steering wires in a transition zone in which one of the two steering wires lies below the other one of the two steering wires; and Tensioning the below one of the two steering wires before the above one of the two steering wires.

Preferably, the method may comprise the steps:

Guiding the two steering wires through guidance holes and fixation holes, in particular provided in a block-shaped protrusion of the wire receiving unit; and Establishing a press-fit connection between the steering wires and the wire receiving unit by inserting mandrels into the fixation holes.

In other words, the present disclosure further relates to a method of assembling an endoscope having a proximal endoscope handle accommodating at least one rotatable operating unit, preferably a handle wheel, a distal tip unit to be inserted into a patient's body cavity and a (flexible) endoscope shaft connecting the endoscope handle and the distal tip unit. The method according to the disclosure comprises the following steps:

Connecting a distal end portion of at least one steering wire to the distal tip unit;

Guiding the at least one steering wire along the flexible shaft to the proximal endoscope handle;

Winding the at least one steering wire for at least one full turn around a wire receiving unit, preferably a wire drum, arranged within the endoscope handle, holding a proximal end portion of the steering wire and being rotatably connected to the operating unit;

Tensioning the at least one steering wire by pulling the loose proximal end portion of the steering wire, preferably with a tensioning force of about 5 N to 50 N, in particular of about 10 N to 20 N;

Fixing the at least one steering wire to the wire receiving unit, preferably by establishing a press-fit connection between the at least one steering wire and the wire drum, in particular by inserting a mandrel into a fixation hole of the wire drum, through which the at least one steering wire is running.

Thereby, it may be useful, when two steering wires are connected to the distal tip unit and guided along the flexible shaft to the proximal endoscope handle, and when one of the two steering wires is wound around the wire receiving unit in a clockwise direction and the other one of the two steering wires is wound around the wire receiving unit in a counter-clockwise direction.

In a beneficial embodiment, the wire receiving unit can comprise a plurality of circumferential grooves, preferably three grooves, in which the two steering wires are accommodated when being wound around the wire receiving unit, so that each of the plurality of grooves is only occupied by one of the two steering wires. Additionally, the two steering wires can overlap when being guided between two respective grooves, and the below one of the two steering wires can be tensioned before the above one of the two steering wires.

BRIEF DESCRIPTION OF FIGURES

The disclosure is explained in more detail below using preferred embodiments and referring to the accompanying figures.

The figures are schematic in nature and serve only to understand the disclosure. Identical elements are marked with the same reference signs. The features of the different embodiments can be exchanged among each other.

DETAILED DESCRIPTION OF A PREFERRED EMBODIMENT

Figure 1:
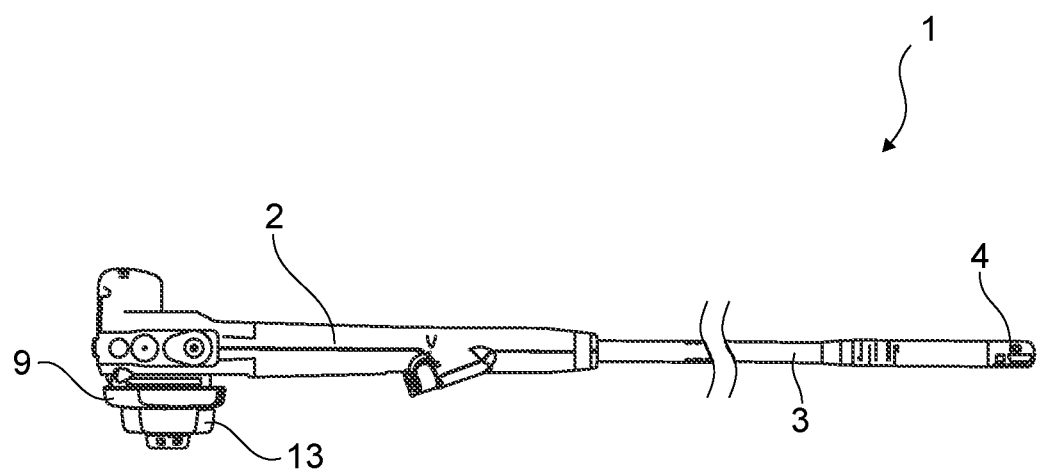
FIG. 1 is a perspective view of an endoscope according to a preferred embodiment.
Figure 2:
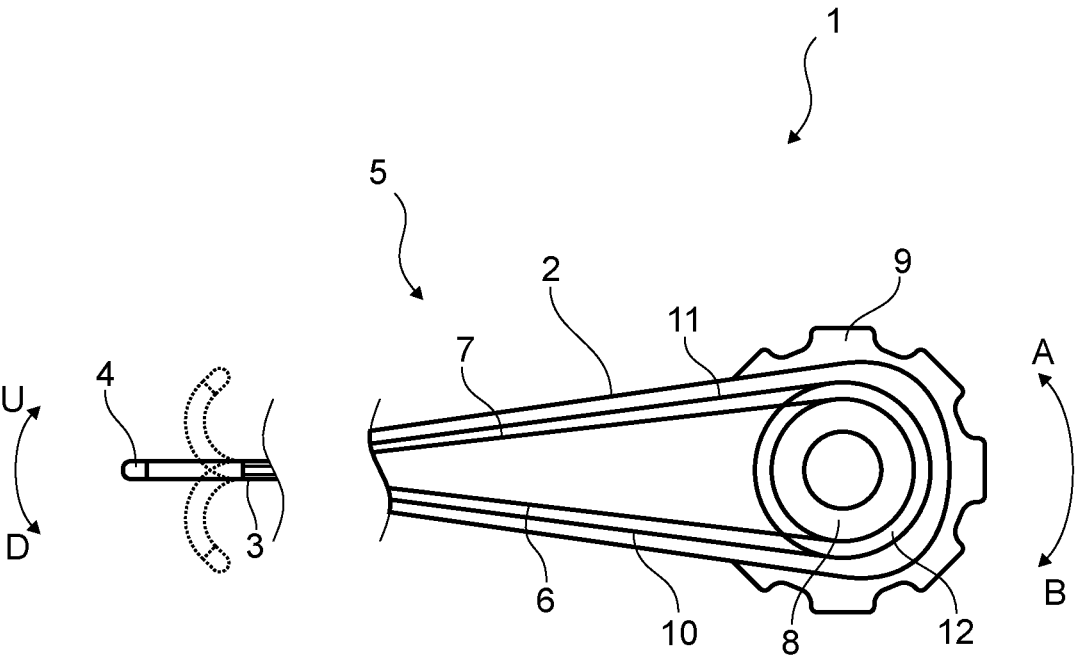
FIG. 2 is a schematic view of the endoscope according to the preferred embodiment.

In FIGS. 1 and 2, an endoscope 1 according to a preferred embodiment is shown. The endoscope 1 is configured preferably as a single use endoscope, and comprises a handle unit 2 designed to be held by an user and a preferably flexible endoscope shaft 3 extending from the handle unit 2 to a distal tip unit 4, which is intended to be inserted into a patient's body cavity. As described below, the handle unit 2 is configured as a housing for accommodating operating parts of the endoscope 1 and comprises two handle shells, only one of which is shown in FIG. 2.

At the distal tip unit 4, image capturing means such as a miniature video camera and illuminating means such as light-emitting diodes or fibre optic light guides connected to a proximal source of light are arranged/installed, such that the patient's body cavity can be illuminated and inspected. Further, the endoscope 1 according to the preferred embodiment may have an internal working channel being formed within the endoscope shaft 3 and guiding a surgical instrument from the proximal end portion into the patient's body cavity, such that the user is able to perform medical operations such as exploration within the patient's body cavity with the surgical instrument. Additionally, at the distal tip unit 4, a rinsing device can be arranged for rinsing or cleaning the image capturing means or parts of the image capturing means.

As indicated in FIG. 2 by dashed lines, the distal tip unit 4 is configured to be tilted/bent/moved by operating a bending, or steering, mechanism 5. The bending mechanism 5 comprises two steering wires 6, 7 being fixed to a wire drum 8, which is accommodated rotatably in the handle unit 2, and being connected to the distal tip unit 4. Further, the wire drum 8 is connected to an operating unit in form of a handle wheel 9, which is arranged on an outside surface of the handle unit 2 and is configured to be turned/rotated by the user. By turning the handle wheel 9, the wire drum 8 rotates thereby pulling and releasing the steering wires 6, 7, so that the distal tip unit 4 tilts according to the direction in which the handle wheel 9 is rotated.

In particular, as can be seen from FIG. 2, if the user rotates the handle wheel 9 counter-clockwise (direction A in FIG. 2), the steering wire 6 is pulled and the steering wire 7 is released, so that the distal tip unit 4 tilts downwards in FIG. 2 (direction D in FIG. 2). Hence, if the user rotates the handle wheel 9 clockwise (direction B in FIG. 2), the steering wire 6 is released, the steering wire 7 is pulled and the distal tip unit 4 tilts upwards (direction U in FIG. 2). In other words, by operating the handle wheel 9 the user is able to tilt the distal tip unit 4 in one bending plane, i.e. the U-D bending plane.

The endoscope 1 according to the preferred embodiment is configured as a two-plane bending endoscope. That means, in addition to the two steering wires 6, 7, the wire drum 8 and the handle wheel 9 for controlling bending in the U-D bending plane, two further steering wires 10, 11 are connected to the distal tip unit 4 and fixed to a second wire drum 12 being accommodated in the handle unit 2. Further, as can be seen in FIG. 1, a second handle wheel 13 is arranged at the handle unit 2 and connected to the second wire drum 12. The steering wires 10, 11 are configured so that the distal tip unit 4 bends in a bending plane perpendicular to the U-D bending plane, i.e. when rotating the handle wheel 13 in a counter-clockwise direction, the steering wire 10 is pulled so that the distal tip unit 4 bends out of the drawing plane of FIG. 2, and when the handle wheel 13 is rotated in a clockwise direction, the steering wire 11 is pulled thereby bending the distal tip unit 4 into the drawing plane of FIG. 2. In other words, by operating the handle wheel 13 the user is able to tilt the distal tip unit 4 in a second bending plane, i.e. the L-R bending plane, perpendicular to the U-D bending plane. It is understood, that the handle wheel 9 can also be configured to control bending in the L-R bending plane, whereas the handle wheel 13 can be configured to control bending in the U-D bending plane. Further, in the endoscope 1 according to the preferred embodiment, the handle wheels 9, 13 and the wire drums 8, 12 are arranged coaxially, i.e. being rotatably around a common rotational axis.

For manually tilting the distal tip unit 4, a so-called deflecting portion (not shown in FIG. 2) is provided between the distal end of the endoscope shaft 3 and the distal tip unit 4 and comprising a number of distally separated segments being hinged to each other such that the deflection portion is bendable/tiltable in accordance with the operation of the handle wheels 9, 13.

Figure 3:
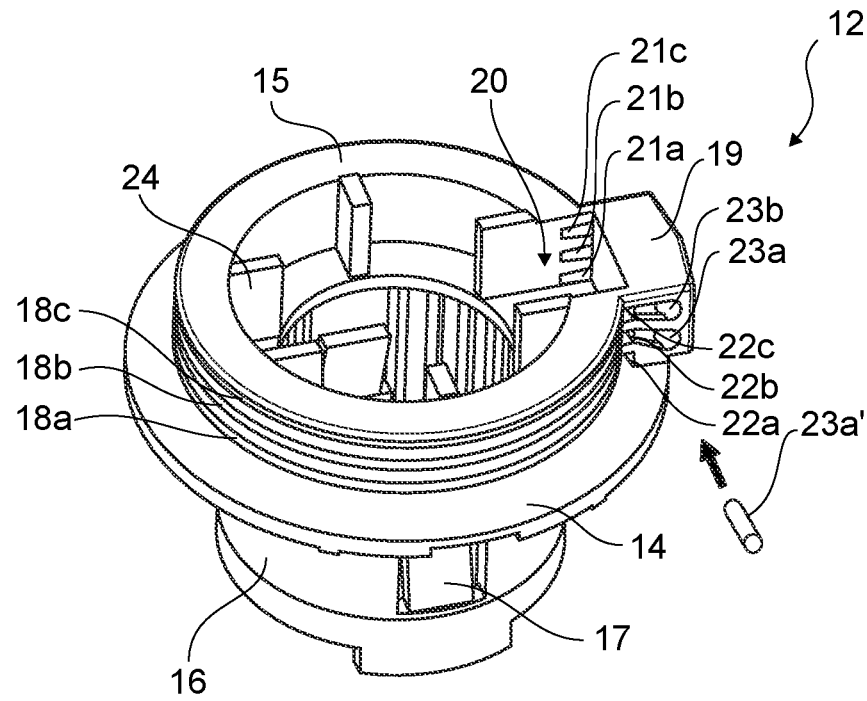
FIG. 3 is a perspective view of a wire drum for the endoscope according to the preferred embodiment.
Figure 4:
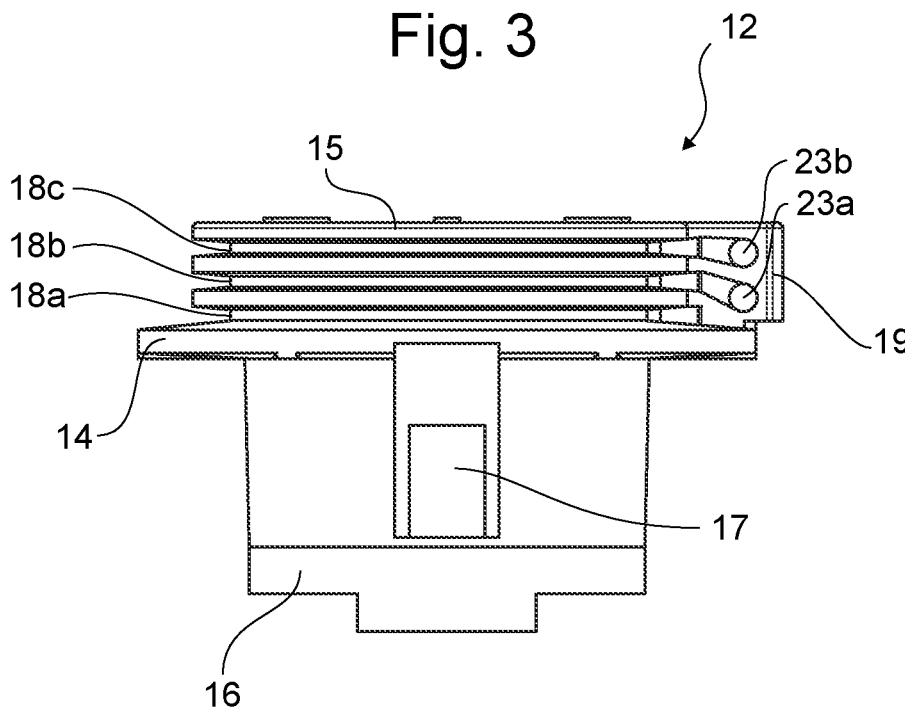
FIG. 4 is a side view of the wire drum of FIG. 3.

FIGS. 3 and 4 show a perspective view and a side view of the wire drum 12. However, both of the wire drums 8, 12 are configured similarly, wherein, as indicated in FIG. 2, the wire drum 12 facing the handle wheels 9, 13 is designed with bigger dimensions in comparison to the wire drum 8. Therefore, the following description is focused on the wire drum 12. However, it is understood, that the configuration and the features described below apply to the wire drum 8, as well, if not stated otherwise explicitly.

The wire drum 12 has a substantial cylindrical shape divided by a circumferential flange portion 14 into an upper or first portion 15 and a lower or second portion 16. On the lower portion 16, two snap fits 17 are arranged diametrically opposed to each other. i.e. on opposite sides of the wire drum, and configured to lock with corresponding recesses formed on a rotating shaft (not shown) being connected with the handle wheel 13, so that a rotation of the handle wheel 13 is transmitted via the rotating shaft and the locking means, i.e. the snap fits 17 interlocking with the recesses, onto the wire drum 12. In other words, the wire drum 12 is connected with the handle wheel 13 by form closure between the snap fits 17 and the recesses formed on the rotating shaft. The snaps/snap fits 17 lock the parts, i.e. the wire drum 12 and the handle wheel 13, together in the axial direction. Radial/rotational locks between the two parts, i.e. the wire drum 12 and the handle wheel 13, are created by multiple splines inside the cylinder/cylindrical lower portion 16, and outside of a (handle) wheel cylinder (not shown).

On the upper portion 15 of the wire drum 12, three grooves 18 are formed, which extend circumferentially around the wire drum 12, in order to guide the steering wires 10, 11, as described below in detail. Thereby, the groove 18a being arranged closest to the flange portion 14 is defined as the "first groove 18a". Accordingly, the groove 18c located at the upper edge of the upper portion 15 is defined as the "third groove 18c" and the groove 18b formed between the first groove 18a and the third groove 18c is defined as the "second groove 18b". Further, a block-shaped fixation protrusion 19 is formed on the upper portion 15. According to the preferred embodiment, the fixation protrusion 19 is arranged at a circumferential position between the two snap fits 17. I.e. when viewing the wire drum 8 from above, the snap fits 17 are arranged at twelve and six o'clock (diametrically opposed), whereas the fixation protrusion 19 is arranged at three o'clock (approximately a quarter circle distanced from the snap fits 17).

As can be seen from FIG. 3, the fixation protrusion 19 is formed as a block being shifted outwards in a radial direction relative to (a remainder of) the upper portion 15, and a hollow space is formed radially inside of the fixation protrusion 19. As described below, this hollow space, where no grooves are formed, functions as a transition zone 20 for the steering wires 10, 11. Further, the three grooves 18 open to the transition zone 20, i.e. six circumferential holes 21a, 21b, 21c, 22a, 22b, 22c are formed at the locations, where the three grooves 18 enter the transition zone 20. Thereby, the two circumferential holes 21a, 22a correspond to the first groove 18a, the circumferential holes 21b, 22b correspond to the second groove 18b and the circumferential holes 21c, 22c correspond to the third groove 18c. Furthermore, two circumferentially extending fixation holes 23a, 23b are formed in the fixation protrusion 19. These fixation holes 23 are implemented as through-holes, i.e. the fixation holes 23 penetrate the fixation protrusion 19 completely in the circumferential direction. Similarly to the grooves 18, the one fixation hole 23a located closer to the flange portion 14 is referred to as the "first fixation hole 23a" and the other fixation hole 23b is referred to as the "second fixation hole 23b". A fixation pin 23a' is also shown, prior to insertion into the first fixation hole 23a.

Additionally, six protrusions 24 are formed protruding from a radially inward facing circumferential surface of the upper portion 15 of the wire drum 12. The number of protrusions 24 may also be different. The number could e.g. be four. These protrusions 24 function as guiding or distancing means for the wire drum 8 and/or the rotating shaft connecting the wire drum 8 with the corresponding handle wheel 9, i.e. the lower portion of the wire drum 8 and/or the rotating shaft assigned to the handle wheel 9 is arranged inside the wire drum 12, wherein the protrusions 24 support the wire drum 12 against the wire drum 8. Therefore, the protrusions 22 are formed only on the upper portion 15 of the wire drum 12.

Figure 6:
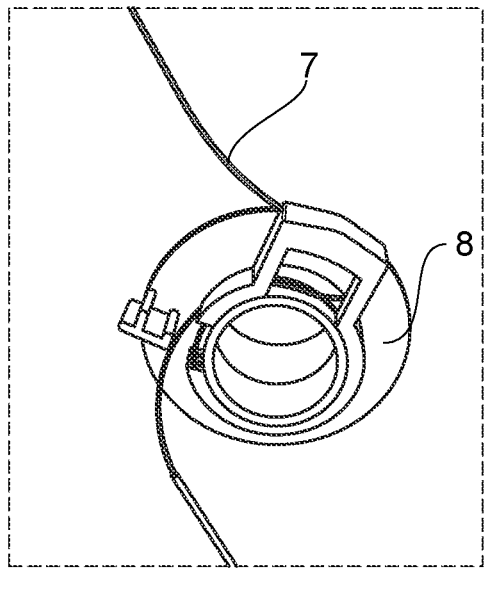
Figure 7:
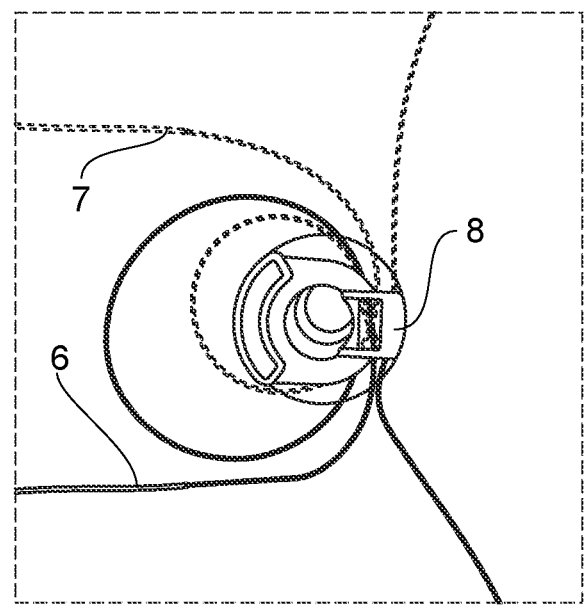
Figure 8:
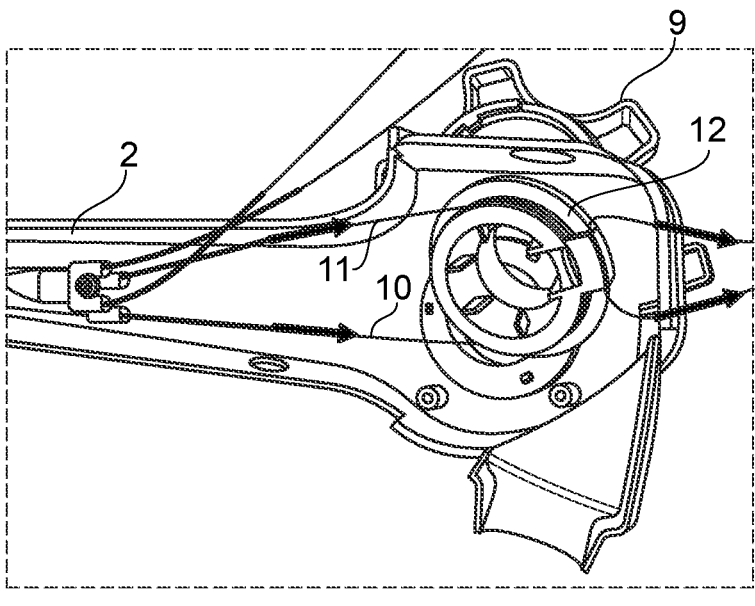

In FIGS. 5 to 8, the endoscope 1 according to the preferred embodiment is shown in various states of assembly. In particular, FIGS. 5 to 8 show an example for mounting steering wires on the wire drum of the endoscope 1 according to the preferred embodiment. If not stated otherwise, the following description of the process of mounting the steering wires can be applied for both of the above described wire drums 8, 12, even if in FIGS. 5 to 7 the wire drum 8 corresponding to the U-D bending plane is shown, whereas FIG. 8 shows the wire drum 12 for bending the distal tip unit 4 in the L-R bending plane. Thus, in the below description, the mounting process is described exemplary for the wire drum 8 corresponding to the U-D bending plane.

Figure 5:
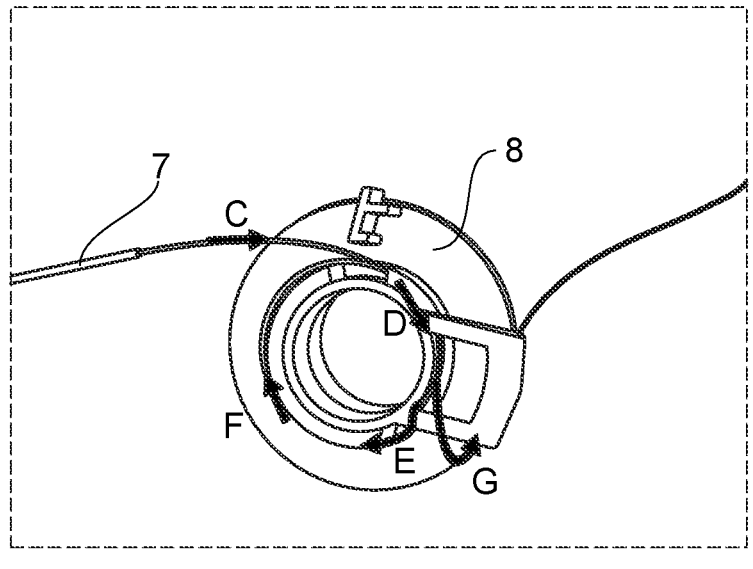
FIGS. 5 to 8 are perspective views of the wire drum for the endoscope according to the preferred embodiment during assembly of the endoscope.

First, as can be seen in FIG. 5, the steering wire 7 runs from the distal tip unit 4 to the wire drum 8 (cf. arrow C in FIG. 5) and is accommodated in the first groove 18a, where it is guided to the transition zone 20 through the circumferential hole 21a (cf. arrow D in FIG. 5) for about a quarter turn. After traversing the transition zone 20, as shown in FIG. 6, the steering wire 7 enters the second groove 18b through the circumferential hole 22b (cf. arrow E in FIG. 5) and is guided within the second groove 18b to the circumferential hole 21b for almost a full turn around the wire drum 8 in the clockwise direction (cf. arrow F in FIG. 5). Through the circumferential hole 21b, the steering wire 7 is guided along and out of the transition zone 20 via the circumferential hole 22b. After exiting the transition zone 20 through the circumferential hole 22b, the steering wire 7 is led back to and through the first fixation hole 23a (cf. arrow G in FIG. 5).

In other words, for mounting the steering wire 7 on the wire drum, a distal end portion of the steering wire 7 is connected to the distal tip unit 4 and a proximal end portion of the steering wire 7 is guided to the wire drum 8, where it is accommodated in the first groove 18a, led through the circumferential hole 21a, via the transition zone 20, through the circumferential hole 22b, within the second groove 18b around the wire drum 8 for almost a full turn in the clockwise direction, through the circumferential hole 21b to the transition zone 20, out of the transition zone 20 through the circumferential hole 22b and back through the first fixation hole 23a in the counter-clockwise direction. I.e. the steering wire 7 is wound up on the wire drum 8 in the clockwise direction for about one and a quarter turns, i.e. approximately 450°.

FIG. 7 shows the wire drum 8 with both of the steering wires 6, 7 being wound up. Thereby, for sake of explanation, the steering wire 7 is shown by a dashed line. As described above, the steering wire 7 is led around the wire drum 8 in the clockwise direction. Accordingly, a distal end portion of the steering wire 6 is connected to the distal tip unit 4 and a proximal end portion of the steering wire 6 is guided to the wire drum 8, where it is accommodated in/enters the first groove 18a. In contrary to the steering wire 7 being accommodated in/entering the first groove 18a at a location corresponding to twelve o'clock when viewing the wire drum 8 from above, the steering wire 6 is accommodated in/enters the first groove 18a at a location diametrically opposite/opposed of the accommodating spot of the steering wire 7, i.e. at six o'clock. Within the first groove 18a, the steering wire 6 is guided in the counter-clockwise direction for about a quarter turn through the circumferential hole 22a to the transition zone 20. Then, the steering wire 6 is led through the circumferential hole 21c out of the transition zone 20 and into the third groove 18c, within which the steering wire 6 is led around the wire drum 6 for almost a full turn in the counter-clockwise direction to the circumferential hole 22c. Through the circumferential hole 22c, the steering wire 6 is led back to the transition zone 20. After exiting the transition zone 20 through the circumferential hole 21c, the steering wire 6 is led back to and through the second fixation hole 23b in the clockwise direction. Thus, the grooves 18 are occupied only by a single steering wire 6, 7.

As described above and shown in FIG. 7, the steering wire 7 is wound up on the wire drum 8 in the clockwise direction and guided within the first groove 18a and the second groove 18b. Further, the steering wire 6 is wound up on the wire drum 8 in the counter-clockwise direction within the first groove 18a and the third groove 18c. At the transition zone 20, both of the steering wires 6, 7 are transitioned from the first groove 18a to the second groove 18b and the third groove 18c, respectively. Thereby, the steering wires 6, 7 cross each other when transitioning at the transition zone 20. In particular, the steering wire 6 being led from the first groove 18a to the third groove 18c lies on top of the steering wire 7.

After mounting the steering wires 6, 7 on the wire drum 8, as described above, the steering wires 6, 7 are tensioned by pulling the loose proximal end portions of the respective steering wires 6, 7, which are guided through the corresponding fixation holes 23a, 23b, with a tensioning force of about 10 to 20 N (indicated by arrows in FIG. 8). When tensioning the steering wires 6, 7, it is important that the steering wire 7 lying below the steering wire 6 at the transition zone 20 is tensioned first. As stated above, the above mounting process is exemplarily described for the wire drum 8 corresponding to the U-D bending plane and holding the steering wires 6, 7, even if in FIG. 8 the wire drum 12 corresponding to the L-R bending plane and holding the steering wires 10, 11 is shown. It is to be understood, that the above-described mounting process is equivalent for both of the wire drums 8, 12 and the respective steering wires, 6, 7 and 10, 11.

After tensioning the steering wires 6, 7, fixation pins/mandrels are inserted in the first fixation hole 23a and the second fixation hole 23b, respectively, in order to fix the steering wires 6, 7, in particular the proximal end portions of the steering wires 6, 7, to the wire drum 8. I.e. the steering wires 6, 7 are fixed to the wire drum 8 by fixation pins being press-fitted in the fixation holes 23a, 23b.

Figure 9:
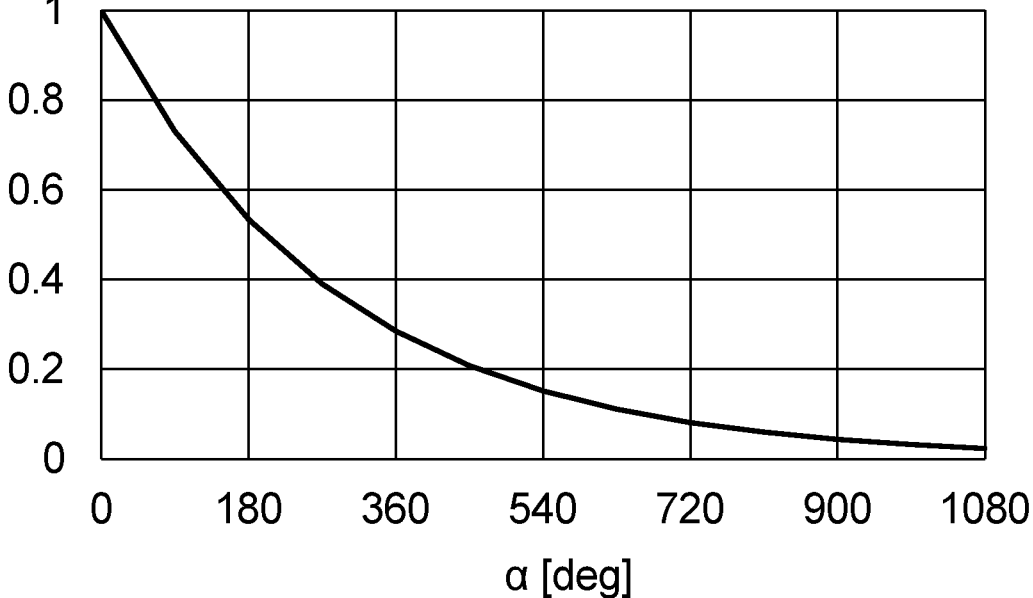
FIG. 9 is a diagram showing relative reduction of a force to be held by fixation pins of the endoscope according to the preferred embodiment due to the Capstan principle.

Due to the steering wires 6, 7 being wound up on the wire drum 8 for about one and a quarter turn, the force to be held by the fixation pins can be reduced according to the Capstan principle. FIG. 9 is a diagram showing the relative reduction of the force to be held by the fixation pins due to the Capstan principle for an estimated friction coefficient $\mu=0.2$, on the abscissa of which is denoted an angle $\alpha$ in degree. The angle $\alpha$ refers to the amount of steering wire being wound up on the respective wire drum, e.g. for a full turn $\alpha=360°$. On the ordinate of the diagram of FIG. 9, the ratio between the force to be held by the fixation pin and a force exerted by the wire due to operation of the handle wheel 9 is depicted. As shown in FIG. 9, for the wire drum 8 being configured for the above described endoscope 1 according to the preferred embodiment, the holding force to be held by the fixation pins is approximately 28% of the force exerted by the steering wires 6, 7 when bending the distal tip unit 4, i.e. rotating the handle wheel 9.

The following items correspond with the original claims.

1. An endoscope (1) comprising: a proximal endoscope handle (2) comprising at least one rotatable operating unit (9; 13), preferably a handle wheel, and at least one wire receiving unit (8; 12), preferably a wire drum, the wire receiving unit (8; 12) being rotatably connected to the operating unit (9; 13); a distal tip unit (4) configured to be inserted into a patient's body cavity; an endoscope shaft (3) connecting the endoscope handle (2) and the distal tip unit (4); and at least one steering wire (6; 7; 10; 11), a proximal end portion of which being held by or fixed to the wire receiving unit (8; 12), the steering wire (6; 7; 10; 11) being guided from the wire receiving unit (8; 12) to the distal tip unit (4) and being configured to be pulled by rotating the operating unit (9; 13), thereby tilting the distal tip unit (4) in at least a defined first direction, wherein the proximal end portion of the at least one steering wire (6; 7; 10; 11) is wound around/on the wire receiving unit (8; 12) for at least one full turn, characterized in that the wire receiving unit (8; 12) comprises a first groove (18a), a second groove (18b) and a third groove (18c), the grooves (18a, 18b, 18c) extending in a circumferential direction of the wire receiving unit (8; 12) and guiding/accommodating two steering wires (6, 7; 10, 11).

2. The endoscope (1) according to item 1, characterized in that two steering wires (6, 7; 10, 11) are wound around/on the wire receiving unit (8; 12), so that when rotating the operating unit (9; 13) in a first circumferential, preferably clockwise, direction one of the two steering wires (6, 7; 10, 11) is pulled and the distal tip unit (4) tilts in the defined first direction and when rotating the operating unit (9; 13) in a second circumferential, preferably counter-clockwise, direction opposite to the first circumferential direction, the other one of the two steering wires (6, 7; 10, 11) is pulled and the distal tip unit (4) tilts in a second defined direction opposite to the first defined direction.

3. The endoscope (1) according to item 2, characterized in that the endoscope handle (2) comprises two operating units (9, 13) and two wire receiving units (8, 12), each of the wire receiving units (8, 12) having two steering wires (6, 7, 10, 11) wound on/around the same and being connected to one of the operating units (9, 13), so that the distal tip unit (4) tilts in a first bending plane defined by the first defined direction and the second defined direction when operating one of the two operating units (9, 13) and the distal tip unit (4) tilts in a second bending plane, preferably perpendicular to the first bending plane, when operating the other one of the two operating units (9, 13).

4. The endoscope (1) according to any one of items 1 to 3, characterized in that the at least one steering wire (6; 7; 10; 11) is fixed to the wire receiving unit (8; 12) via a press fit connection.

5. The endoscope (1) according to item 4, characterized in that at least one, preferably circumferentially extending, fixation hole (23a; 23b) is formed on the wire receiving unit (8; 12), in particular in a block-shaped fixation protrusion (19), the at least one steering wire (6; 7; 10; 11) being fixed to the wire receiving unit (8; 12) by means of a mandrel inserted in said fixation hole (23a; 23b) such that the at least one steering wire (6; 7; 10; 11) and the mandrel form the press fit connection.

6. The endoscope (1) according to any one of items 1 to 5, characterized in that the first groove (18a) is arranged closest to a flange portion (14) of the wire receiving unit (8; 12), the third groove (18c) is arranged farthermost from the flange portion (14), and the second groove (18b) is arranged between the first groove (18a) and the third groove (18c), wherein one of the two steering wires (6, 7; 10, 11) runs around the wire receiving unit (8; 12) within the first groove (18a) and the second groove (18b) and the other one of the two steering wires (6, 7; 10, 11) runs around the wire receiving unit (8; 12) within the first groove (18a) and the third groove (18c).

7. The endoscope (1) according to any one of items 1 to 5, characterized in that the two steering wires (6, 7; 10, 11) both enter the same circumferential groove among the first groove (18a), the second groove (18b) and the third groove (18c), in particular at diametrically opposed positions of the respective circumferential groove, and transition/transfer to their respective own groove among the first groove (18a), the second groove (18b) and the third groove (18c) when wound around/on the wire receiving unit (8:12).

8. The endoscope (1) according to any one of items 1 to 5, characterized in that one of the two steering wires (6, 7; 10, 11) enters the first groove (18a) at a first position, runs around the wire receiving unit (8; 12) for a quarter turn within the first groove (18a), transitions to the second groove (18b) and runs within the second groove (18b) for a full turn before being fixed to the wire receiving unit (8; 12), and the other one of the two steering wires (6, 7; 10, 11) enters the first groove (18a) at a second position, preferably diametrically opposed to the first position, runs around the wire receiving unit (8; 12) for a quarter turn within the first groove (18a), transitions to the third groove (18c) and runs within the third groove (18c) for a full turn before being fixed to the wire receiving unit (8; 12).

9. The endoscope (1) according to item 8, characterized in that the one of the two steering wires (6, 7; 10, 11) and the other one of the two steering wires (6, 7; 10, 11) transition from the first groove (18a) to the second groove (18b) or the third groove (18c), respectively, within a transition zone (20) being formed radially inside of a fixation protrusion (19).

10. A method of assembling an endoscope (1) having: a proximal endoscope handle (2) comprising at least one rotatable operating unit (9; 13), preferably a handle wheel, and at least one wire receiving unit (8; 12), preferably a wire drum, comprising a first groove (18a), a second groove (18b) and a third groove (18c), the grooves (18a, 18b, 18c) extending in a circumferential direction of the wire receiving unit (8; 12) and guiding/accommodating two steering wires (6, 7; 10, 11); a distal tip unit (4) configured to be inserted into a patient's body cavity; and an endoscope shaft (3) connecting the endoscope handle (2) and the distal tip unit (4); the method comprising the following steps: Connecting a distal end portion of each of the two steering wires (6; 7:10; 11) to the distal tip unit (4); Guiding each of the two steering wires (6; 7; 10; 11) along the endoscope shaft (3) to the endoscope handle (2); Winding each of the two steering wires (6; 7; 10; 11) for at least one full turn around the wire receiving unit (8; 12); Tensioning each of the two steering wires (6; 7; 10; 11) by pulling the proximal end portion of the steering wire (6:7; 10; 11); Fixing each of the two steering wires (6; 7; 10; 11) to the wire receiving unit (8; 12).

11. The method according to item 10, further comprising the steps: Winding one of the two steering wires (6, 7; 10, 11) around the wire receiving unit (8; 12) in a clockwise direction; and Winding the other one of the two steering wires (6, 7; 10, 11) around the wire receiving unit (8; 12) in a counter-clockwise direction.

12. The method according to item 11, further comprising the steps: Introducing the two steering wires (6, 7; 10, 11) in the first circumferential groove (18a) provided on the wire receiving unit (8; 12); Transferring one of the two steering wires (6, 7; 10, 11) from the first circumferential groove (18a) into the second circumferential groove (18b); Transferring the other one of the two steering wires (6, 7; 10, 11) from the first circumferential groove (18a) into the third circumferential groove (18c); Winding the one of the two steering wires (6, 7; 10, 11) around the second circumferential groove (18b); and Winding the other one of the two steering wires (6, 7; 10, 11) around the third circumferential groove (18c).

13. The method according to item 11 or 12, further comprising the steps: Overlapping the two steering wires (6, 7; 10, 11) in a transition zone (20) in which one of the two steering wires (6, 7; 10, 11) lies below the other one of the two steering wires (6, 7; 10, 11); and Tensioning the below one of the two steering wires (6, 7; 10, 11) before the above one of the two steering wires (6, 7; 10, 11).

14. The method according to any one of items 11 to 13, further comprising the steps: Guiding the two steering wires (6, 7; 10, 11) through guidance holes (21a, 21b, 21c, 22a, 22b, 22c) and fixation holes (23a, 23b), in particular provided in a block-shaped protrusion (19) of the wire receiving unit (8; 12); and Establishing a press-fit connection between the steering wires (6, 7; 10, 11) and the wire receiving unit (8; 12) by inserting mandrels into the fixation holes (23a, 23b).

What is claimed is:

1. An endoscope comprising:
a handle comprising a first operating unit and a first wire drum rotatably connected to the first operating unit, the first wire drum including grooves, a fixation protrusion, and a hollow space, the grooves extending in a circumferential direction of the first wire drum and including a first groove, a second groove and a third groove, each of the grooves beginning at a first hole facing the hollow space and ending at a second hole facing the hollow space, the first hole facing the second hole with the hollow space therebetween forming a transition zone, the fixation protrusion extending radially outwardly from the hollow space;
a distal tip unit;
an endoscope shaft connecting the handle and the distal tip unit; and
a first steering wire proximal end portion wound around/on the first wire drum for at least one full turn, rotation of the first operating unit in a first circumferential direction pulling the first steering wire proximal end portion and thus steering the distal tip unit in a first direction; and
a second steering wire proximal end portion wound around/on the first wire drum for at least one full turn, a rotation opposite the first circumferential direction of the first operating unit pulling the second steering wire proximal end portion and thus steering the distal tip unit in a second direction different than the first direction,
wherein the second groove is arranged laterally from, and between, the first groove and the third groove,
wherein the grooves are interrupted at the transition zone and
wherein the transition zone and the fixation protrusion are radially aligned.

2. The endoscope of claim 1, wherein rotation of the first operating unit in the first circumferential direction pulls on the first steering wire proximal end portion and releases tension on the second steering wire proximal end portion, and wherein rotation of the first operating unit opposite the first circumferential direction pulls on the second steering wire proximal end portion and releases tension on the first steering wire proximal end portion.

3. The endoscope of claim 1, wherein rotation of the first operating unit steers the distal tip unit in a first bending plane defined by the first direction and the second direction.

4. The endoscope of claim 1, wherein the handle further comprises a second operating unit and a second wire drum rotatably connected to the second operating unit, wherein the endoscope further comprises two steering wire proximal end portions wound on/around the second wire drum for at least one full turn, wherein clockwise rotation of the second operating unit pulls on one of the two steering wire proximal end portions thus steering the distal tip unit in a third direction, and wherein counter-clockwise rotation of the second operating unit pulls on the other of the two steering wire proximal end portions thus steering the distal tip unit in a fourth direction different than the third direction.

5. The endoscope of claim 4, wherein rotation of the first operating unit steers the distal tip unit in a first bending plane defined by the first direction and the second direction, and wherein rotation of the second operating unit steers the distal tip unit in a second bending plane defined by the third direction and the fourth direction.

6. The endoscope of claim 5, wherein the first bending plane is perpendicular to the second bending plane.

7. The endoscope of claim 1, wherein the first steering wire proximal end portion is affixed to the first wire drum via a first press fit connection.

8. An endoscope comprising:
a handle comprising a first operating unit and a first wire drum rotatably connected to the first operating unit, the first wire drum including grooves, a fixation protrusion, and a hollow space, the grooves extending in a circumferential direction of the first wire drum and including a first groove, a second groove and a third groove, each of the grooves beginning at a first hole facing the hollow space and ending at a second hole facing the hollow space, the first hole facing the second hole with the hollow space therebetween forming a transition zone, the fixation protrusion extending radially outwardly from the hollow space;
a distal tip unit;
an endoscope shaft connecting the handle and the distal tip unit;
a first steering wire proximal end portion wound around/on the first wire drum for at least one full turn, rotation of the first operating unit in a first circumferential direction pulling the first steering wire proximal end portion and thus steering the distal tip unit in a first direction;
a second steering wire proximal end portion wound around/on the first wire drum for at least one full turn, a rotation opposite the first circumferential direction of the first operating unit pulling the second steering wire proximal end portion and thus steering the distal tip unit in a second direction different than the first direction; and
a first fixation pin,
wherein the first steering wire proximal end portion is affixed to the first wire drum via a first press fit connection,
wherein the fixation protrusion comprises a first fixation hole having an internal surface, and
wherein the first press fit connection is formed by the first fixation pin pressing the first steering wire proximal end portion against the internal surface of the fixation hole.

9. The endoscope of claim 8, wherein the fixation hole extends in a circumferential direction.

10. The endoscope of claim 7, wherein the second steering wire proximal end portion is affixed to the first wire drum via a second press fit connection.

11. The endoscope of claim 1, wherein the first steering wire proximal end portion and the second steering wire proximal end portion enter one of the grooves before wounding around/on others of the grooves.

12. The endoscope of claim 11, wherein the first steering wire proximal end portion and the second steering wire proximal end portion enter the one of the grooves at diametrically opposite sides of the first wire drum.

13. The endoscope of claim 1, wherein the first steering wire proximal end portion runs around the first wire drum within the first groove and the second groove, and wherein the second steering wire proximal end portion runs around the first wire drum within the first groove and the third groove.

14. The endoscope of claim 13, wherein the first steering wire proximal end portion and the second steering wire proximal end portion enter the first groove at diametrically opposite sides of the first wire drum.

15. The endoscope of claim 13, wherein at the transition zone the first steering wire proximal end portion crosses over from the first groove to the second groove and the second steering wire proximal end portion crosses over from the first groove to the third groove.

16. An endoscope comprising:
   a handle comprising a first operating unit and a first wire drum rotatably connected to the first operating unit, the first wire drum including grooves extending in a circumferential direction of the first wire drum, and the grooves including a first groove, a second groove and a third groove;
   a distal tip unit;
   an endoscope shaft connecting the handle and the distal tip unit; and
   a first steering wire proximal end portion wound around/on the first wire drum for at least one full turn, rotation of the first operating unit in a first circumferential direction pulling the first steering wire proximal end portion and thus steering the distal tip unit in a first direction; and
   a second steering wire proximal end portion wound around/on the first wire drum for at least one full turn, a rotation opposite the first circumferential direction of the first operating unit pulling the second steering wire proximal end portion and thus steering the distal tip unit in a second direction different than the first direction,
   wherein the first steering wire proximal end portion runs around the first wire drum within the first groove and the second groove, and wherein the second steering wire proximal end portion runs around the first wire drum within the first groove and the third groove,
   wherein the first wire drum comprises a transition zone, and wherein at the transition zone the first steering wire proximal end portion crosses over from the first groove to the second groove and the second steering wire proximal end portion crosses over from the first groove to the third groove, and
   wherein the second groove is arranged laterally from, and between, the first groove and the third groove.

17. The endoscope of claim 16, wherein the grooves extend a radial distance from a longitudinal axis of the first wire drum, the radial distance being the same for each of the grooves.

18. The endoscope of claim 15, wherein the grooves are interrupted at the transition zone.

19. The endoscope of claim 15, wherein the first steering wire proximal end portion is affixed to the first wire drum via a first press fit connection, the fixation protrusion having a first fixation hole, and wherein the first press fit connection is formed in the first fixation hole.

20. The endoscope of claim 19, wherein the first steering wire proximal end portion enters the transition zone a first time to cross over from the first groove to the second groove, then wraps around the second groove before entering the transition zone a second time, then exits the transition zone and enters the first fixation hole.

21. The endoscope of claim 1, wherein the first steering wire proximal end portion enters the first groove at a first position, runs around the first wire drum for a quarter turn within the first groove, transitions to the second groove and runs within the second groove for a full turn before being fixed to the first wire drum, and the second steering wire proximal end portion enters the first groove at a second position, runs around the first wire drum for a quarter turn within the first groove, transitions to the third groove and runs within the third groove for a full turn before being fixed to the first wire drum.

22. The endoscope of claim 1, wherein at the transition zone the first steering wire proximal end portion crosses over from the first groove to the second groove and the second steering wire proximal end portion crosses over from the first groove to the third groove.

23. An endoscope comprising:
   a handle comprising a first operating unit and a first wire drum rotatably connected to the first operating unit, the first wire drum including grooves extending in a circumferential direction of the first wire drum, and the grooves including a first groove, a second groove and a third groove;
   a distal tip unit;
   an endoscope shaft connecting the handle and the distal tip unit; and
   a first steering wire proximal end portion wound around/on the first wire drum for at least one full turn, rotation of the first operating unit in a first circumferential direction pulling the first steering wire proximal end portion and thus steering the distal tip unit in a first direction; and
   a second steering wire proximal end portion wound around/on the first wire drum for at least one full turn, a rotation opposite the first circumferential direction of the first operating unit pulling the second steering wire proximal end portion and thus steering the distal tip unit in a second direction different than the first direction,
   wherein the first steering wire proximal end portion enters the first groove at a first position, runs around the first wire drum for a quarter turn within the first groove, transitions to the second groove and runs within the second groove for a full turn before being fixed to the first wire drum, and the second steering wire proximal end portion enters the first groove at a second position, runs around the first wire drum for a quarter turn within the first groove, transitions to the third groove and runs within the third groove for a full turn before being fixed to the first wire drum wherein the first wire drum comprises a transition zone and a fixation protrusion, and wherein at the transition zone the first steering wire proximal end portion crosses over from the first groove to the second groove and the second steering wire proximal end portion crosses over from the first groove to the third groove, and wherein the transition zone and the fixation protrusion are radially aligned.

\* \* \* \* \*